United States Patent
Temsamani et al.

(10) Patent No.: US 7,527,792 B1
(45) Date of Patent: May 5, 2009

(54) PHARMACEUTICAL COMPOSITION COMPRISING AN ANTI-CANCER AND AT LEAST A PEPTIDE

(75) Inventors: Jamal Temsamani, Nîmes (FR); Michel Kaczorek, Montferrier sur Lez (FR)

(73) Assignee: Synt : EM, Nimes (FR)

( * ) Notice: Subject to any disclaimer, the term of this patent is extended or adjusted under 35 U.S.C. 154(b) by 0 days.

(21) Appl. No.: 09/856,940

(22) PCT Filed: Nov. 26, 1999

(86) PCT No.: PCT/FR99/02939

§ 371 (c)(1),
(2), (4) Date: Dec. 6, 2001

(87) PCT Pub. No.: WO00/32237

PCT Pub. Date: Jun. 8, 2000

(30) Foreign Application Priority Data

Nov. 30, 1998 (FR) .................................. 98/15073

(51) Int. Cl.
*A61K 39/38* (2006.01)

(52) U.S. Cl. .................................................. 424/184.1
(58) Field of Classification Search ............... 424/184.1
See application file for complete search history.

(56) References Cited

U.S. PATENT DOCUMENTS 5,608,039 A * 3/1997 Pastan et al. ............. 530/387.3
2006/0293242 A1  12/2006 Temsamani et al.

OTHER PUBLICATIONS

Gura (Science, 1997, 278:1041-1042.).*
U.S. Appl. No. 09/856,940, filed Dec. 6, 2001, Temsamani, et al.
U.S. Appl. No. 10/490,357, filed Aug. 20, 2004, Temsamani, et al.

* cited by examiner

*Primary Examiner*—Sean E Aeder
(74) *Attorney, Agent, or Firm*—Oblon, Spivak, McClelland, Maier & Neustadt, P.C.

(57) ABSTRACT

The invention concerns a pharmaceutical composition for treating and/or preventing cancer comprising at least an anti-cancer agent, characterised in that said anticancer agent is associated in the composition with at least a peptide capable of carrying said agent into the cancer cells and prevent the occurrence of chemoresistance to said agent.

1 Claim, 5 Drawing Sheets

Figure 1: Preparation of doxorubicin-Succ-peptides

Figure 2: Preparation of doxorubicin-SMP-3MP-peptides

SEQUENCE LISTING

<160> NUMBER OF SEQ ID NOS: 17

<210> SEQ ID NO 1
<211> LENGTH: 18
<212> TYPE: PRT
<213> ORGANISM: Sus
<220> FEATURE:
<221> NAME/KEY: PEPTIDE
<222> LOCATION: (1)..(18)
<223> OTHER INFORMATION: Protegrin PG1

<400> SEQUENCE: 1

Arg Gly Gly Arg Leu Cys Tyr Cys Arg Arg Arg Phe Cys Val Cys Val
1               5                   10                  15

Gly Arg

<210> SEQ ID NO 2
<211> LENGTH: 16
<212> TYPE: PRT
<213> ORGANISM: Sus
<220> FEATURE:
<221> NAME/KEY: PEPTIDE
<222> LOCATION: (1)..(16)
<223> OTHER INFORMATION: Protegrin PG2

<400> SEQUENCE: 2

Arg Gly Gly Arg Leu Cys Tyr Cys Arg Arg Arg Phe Cys Ile Cys Val
1               5                   10                  15

<210> SEQ ID NO 3
<211> LENGTH: 18
<212> TYPE: PRT
<213> ORGANISM: Sus
<220> FEATURE:
<221> NAME/KEY: PEPTIDE
<222> LOCATION: (1)..(18)
<223> OTHER INFORMATION: Protegrin PG3

<400> SEQUENCE: 3

Arg Gly Gly Gly Leu Cys Tyr Cys Arg Arg Arg Phe Cys Val Cys Val
1               5                   10                  15

Gly Arg

<210> SEQ ID NO 4
<211> LENGTH: 18
<212> TYPE: PRT
<213> ORGANISM: Sus
<220> FEATURE:
<221> NAME/KEY: PEPTIDE
<222> LOCATION: (1)..(18)
<223> OTHER INFORMATION: Protegrin PG4

<400> SEQUENCE: 4

Arg Gly Gly Arg Leu Cys Tyr Cys Arg Gly Trp Ile Cys Phe Cys Val
1               5                   10                  15

Gly Arg

<210> SEQ ID NO 5
<211> LENGTH: 18
<212> TYPE: PRT
<213> ORGANISM: Sus
<220> FEATURE:
<221> NAME/KEY: PEPTIDE
<222> LOCATION: (1)..(18)
<223> OTHER INFORMATION: Protegrin PG5

<400> SEQUENCE: 5

Arg Gly Gly Arg Leu Cys Tyr Cys Arg Pro Arg Phe Cys Val Cys Val
1               5                   10                  15

Gly Arg

<210> SEQ ID NO 6
<211> LENGTH: 18
<212> TYPE: PRT
<213> ORGANISM: Limmulus polyphemus
<220> FEATURE:
<221> NAME/KEY: PEPTIDE
<222> LOCATION: (1)..(18)
<223> OTHER INFORMATION: Polyphemusin P1

<400> SEQUENCE: 6

Arg Arg Trp Cys Phe Arg Val Cys Tyr Arg Gly Phe Cys Tyr Arg Lys
1               5                   10                  15

Cys Arg

<210> SEQ ID NO 7
<211> LENGTH: 18
<212> TYPE: PRT
<213> ORGANISM: Limmulus polyphemus
<220> FEATURE:
<221> NAME/KEY: PEPTIDE

```
<222> LOCATION: (1)..(18)
<223> OTHER INFORMATION: Polyphemusin P2

<400> SEQUENCE: 7

Arg Arg Trp Cys Phe Arg Val Cys Tyr Lys Gly Phe Cys Tyr Arg Lys
1               5                   10                  15

Cys Arg

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(16)
<223> OTHER INFORMATION: Xaa is any natural or non-natural amino acid
      including D configuration amino acid and 6 to 10 Xaa amino acids
      each are selected from Ala, Val, Leu, Ile, Pro, Phe, Try, Tyr, and
      Met

<400> SEQUENCE: 8

Xaa Xaa Xaa Xaa Xaa Trp Xaa Xaa Xaa Xaa Xaa Xaa Xaa Xaa Xaa Xaa
1               5                   10                  15

<210> SEQ ID NO 9
<211> LENGTH: 18
<212> TYPE: PRT
<213> ORGANISM: Atrificial Sequence
<220> FEATURE:
<221> NAME/KEY: PEPTIDE
<222> LOCATION: (1)..(18)
<223> OTHER INFORMATION: Synthetic peptide of formula (II)
<220> FEATURE:
<221> NAME/KEY: MISC_FEATURE
<222> LOCATION: (1)..(1)
<223> OTHER INFORMATION: Asx represents a natural or non-natural amino
      acid, including an amino acid with D configuration, in which the
      side chain carries a basic group
<220> FEATURE:
<221> NAME/KEY: MISC_FEATURE
<222> LOCATION: (2)..(2)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (3)..(3)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (4)..(4)
<223> OTHER INFORMATION: Asx represents a natural or non-natural amino
      acid, including an amino acid with D configuration, in which the
      side chain carries a basic group
<220> FEATURE:
<221> NAME/KEY: MISC_FEATURE
<222> LOCATION: (5)..(5)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (6)..(6)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (7)..(7)
<223> OTHER INFORMATION: Xaa represents a natural or non-natural amino
``` acid, including amino acid with D configuration, in which the side
chain carries an aliphatic or aromatic group
<220> FEATURE:
<221> NAME/KEY: MISC_FEATURE
<222> LOCATION: (8)..(8)
<223> OTHER INFORMATION: Xaa represents a natural or non-natural amino
acid, including amino acid with D configuration, in which the side
chain carries an aliphatic or aromatic group
<220> FEATURE:
<221> NAME/KEY: MISC_FEATURE
<222> LOCATION: (9)..(9)
<223> OTHER INFORMATION: Asx represents a natural or non-natural amino
acid, including an amino acid with D configuration, in which the
side chain carries a basic group
<220> FEATURE:
<221> NAME/KEY: MISC_FEATURE
<222> LOCATION: (10)..(10)
<223> OTHER INFORMATION: Asx represents a natural or non-natural amino
acid, including an amino acid with D configuration, in which the
side chain carries a basic group
<220> FEATURE:
<221> NAME/KEY: MISC_FEATURE
<222> LOCATION: (11)..(11)
<223> OTHER INFORMATION: Asx represents a natural or non-natural amino
acid, including an amino acid with D configuration, in which the
side chain carries a basic group
<220> FEATURE:
<221> NAME/KEY: MISC_FEATURE
<222> LOCATION: (12)..(12)
<223> OTHER INFORMATION: Xaa represents a natural or non-natural amino
acid, including amino acid with D configuration, in which the side
chain carries an aliphatic or aromatic group
<220> FEATURE:
<221> NAME/KEY: MISC_FEATURE
<222> LOCATION: (13)..(13)
<223> OTHER INFORMATION: Xaa represents a natural or non-natural amino
acid, including amino acid with D configuration, in which the side
chain carries an aliphatic or aromatic group
<220> FEATURE:
<221> NAME/KEY: MISC_FEATURE
<222> LOCATION: (14)..(14)
<223> OTHER INFORMATION: Xaa represents a natural or non-natural amino
acid, including amino acid with D configuration, in which the side
chain carries an aliphatic or aromatic group
<220> FEATURE:
<221> NAME/KEY: MISC_FEATURE
<222> LOCATION: (15)..(15)
<223> OTHER INFORMATION: Xaa represents a natural or non-natural amino
acid, including amino acid with D configuration, in which the side
chain carries an aliphatic or aromatic group
<220> FEATURE:
<221> NAME/KEY: MISC_FEATURE
<222> LOCATION: (16)..(16)
<223> OTHER INFORMATION: Xaa represents a natural or non-natural amino
acid, including amino acid with D configuration, in which the side
chain carries an aliphatic or aromatic group
<220> FEATURE:
<221> NAME/KEY: MISC_FEATURE
<222> LOCATION: (17)..(17)
<223> OTHER INFORMATION: Xaa represents a natural or non-natural amino
acid, including amino acid with D configuration, in which the side
chain carries an aliphatic or aromatic group
<220> FEATURE:
<221> NAME/KEY: MISC_FEATURE
<222> LOCATION: (18)..(18)
<223> OTHER INFORMATION: Asx represents a natural or non-natural amino
acid, including an amino acid with D configuration, in which the
side chain carries a basic group

<400> SEQUENCE: 9

Asx Xaa Xaa Asx Xaa Xaa Xaa Xaa Asx Asx Asx Xaa Xaa Xaa Xaa Xaa
1               5                   10                  15

Xaa Asx

<210> SEQ ID NO 10
<211> LENGTH: 17

```
<212> TYPE: PRT
<213> ORGANISM: Atrificial Sequence
<220> FEATURE:
<221> NAME/KEY: MISC_FEATURE
<222> LOCATION: (1)..(1)
<223> OTHER INFORMATION: Asx represents a natural or non-natural amino
      acid, including an amino acid with D configuration, in which the
      side chain carries a basic group
<220> FEATURE:
<221> NAME/KEY: PEPTIDE
<222> LOCATION: (1)..(17)
<223> OTHER INFORMATION: Synthetic Peptide of formula (III)
<220> FEATURE:
<221> NAME/KEY: MISC_FEATURE
<222> LOCATION: (2)..(2)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (3)..(3)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (4)..(4)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (5)..(5)
<223> OTHER INFORMATION: Asx represents a natural or non-natural amino
      acid, including an amino acid with D configuration, in which the
      side chain carries a basic group
<220> FEATURE:
<221> NAME/KEY: MISC_FEATURE
<222> LOCATION: (6)..(6)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (7)..(7)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (8)..(8)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (9)..(9)
<223> OTHER INFORMATION: Asx represents a natural or non-natural amino
      acid, including an amino acid with D configuration, in which the
      side chain carries a basic group
<220> FEATURE:
<221> NAME/KEY: MISC_FEATURE
<222> LOCATION: (10)..(10)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (11)..(11)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (12)..(12)
<223> OTHER INFORMATION: Xaa represents a natural or non-natural amino
      acid, including amino acid with D configuration, in which the side
      chain carries an aliphatic or aromatic group
<220> FEATURE:
```

```
<221> NAME/KEY: MISC_FEATURE
<222> LOCATION: (13)..(13)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (14)..(14)
<223> OTHER INFORMATION: Asx represents a natural or non-natural amino
      acid, including an amino acid with D configuration, in which the
      side chain carries a basic group
<220> FEATURE:
<221> NAME/KEY: MISC_FEATURE
<222> LOCATION: (15)..(15)
<223> OTHER INFORMATION: Asx represents a natural or non-natural amino
      acid, including an amino acid with D configuration, in which the
      side chain carries a basic group
<220> FEATURE:
<221> NAME/KEY: MISC_FEATURE
<222> LOCATION: (16)..(16)
<223> OTHER INFORMATION: Xaa represents a natural or non-natural amino
      acid, including amino acid with D configuration, in which the side
      chain carries an aliphatic or aromatic group
<220> FEATURE:
<221> NAME/KEY: MISC_FEATURE
<222> LOCATION: (17)..(17)
<223> OTHER INFORMATION: Asx represents a natural or non-natural amino
      acid, including an amino acid with D configuration, in which the
      side chain carries a basic group

<400> SEQUENCE: 10

Asx Xaa Xaa Xaa Asx Xaa Xaa Xaa Asx Xaa Xaa Xaa Xaa Asx Asx Xaa
1               5                   10                  15

Asx

<210> SEQ ID NO 11
<211> LENGTH: 18
<212> TYPE: PRT
<213> ORGANISM: Atrificial Sequence
<220> FEATURE:
<221> NAME/KEY: PEPTIDE
<222> LOCATION: (1)..(18)
<223> OTHER INFORMATION: Synthetic peptide

<400> SEQUENCE: 11

Arg Gly Gly Arg Leu Ser Tyr Ser Arg Arg Arg Phe Ser Thr Ser Thr
1               5                   10                  15

Gly Arg

<210> SEQ ID NO 12
<211> LENGTH: 18
<212> TYPE: PRT
<213> ORGANISM: Atrificial Sequence
<220> FEATURE:
<221> NAME/KEY: PEPTIDE
<222> LOCATION: (1)..(18)
<223> OTHER INFORMATION: Synthetic peptide

<400> SEQUENCE: 12

Arg Gly Gly Arg Leu Ser Tyr Ser Arg Arg Arg Phe Ser Val Ser Val
1               5                   10                  15

Gly Arg

<210> SEQ ID NO 13
<211> LENGTH: 17
<212> TYPE: PRT
<213> ORGANISM: Atrificial Sequence
<220> FEATURE:
<221> NAME/KEY: PEPTIDE
<222> LOCATION: (1)..(17)
```

-continued

<223> OTHER INFORMATION: Synthetic peptide

<400> SEQUENCE: 13

Lys Trp Ser Phe Arg Val Ser Tyr Arg Gly Ile Ser Tyr Arg Arg Ser
1               5                   10                  15
Arg

<210> SEQ ID NO 14
<211> LENGTH: 10
<212> TYPE: PRT
<213> ORGANISM: Atrificial Sequence
<220> FEATURE:
<221> NAME/KEY: PEPTIDE
<222> LOCATION: (1)..(10)
<223> OTHER INFORMATION: Synthetic peptide

<400> SEQUENCE: 14

Arg Arg Leu Ser Tyr Ser Arg Arg Arg Phe
1               5                   10

<210> SEQ ID NO 15
<211> LENGTH: 16
<212> TYPE: PRT
<213> ORGANISM: Atrificial Sequence
<220> FEATURE:
<221> NAME/KEY: PEPTIDE
<222> LOCATION: (1)..(16)
<223> OTHER INFORMATION: Synthetic peptide

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 17
<212> TYPE: PRT
<213> ORGANISM: Atrificial Sequence
<220> FEATURE:
<221> NAME/KEY: PEPTIDE
<222> LOCATION: (1)..(17)
<223> OTHER INFORMATION: Synthetic peptide

<400> SEQUENCE: 16

Cys Glu Asn Ile Lys Ile Trp Leu Ser Leu Arg Ser Tyr Leu Lys Arg
1               5                   10                  15
Arg

<210> SEQ ID NO 17
<211> LENGTH: 18
<212> TYPE: PRT
<213> ORGANISM: Atrificial Sequence
<220> FEATURE:
<221> NAME/KEY: PEPTIDE
<222> LOCATION: (1)..(18)
<223> OTHER INFORMATION: Synthetic peptide

<400> SEQUENCE: 17

Arg Gly Gly Arg Leu Ala Tyr Leu Arg Arg Arg Trp Ala Val Leu Val
1               5                   10                  15
Gly Arg

PHARMACEUTICAL COMPOSITION COMPRISING AN ANTI-CANCER AND AT LEAST A PEPTIDE

The present invention relates to the use of peptides to carry anti-cancer agents in applications for treating and/or preventing cancer, more particularly in the field of chemoresistance.

A significant problem encountered in the pharmacology of anti-cancer products consists of the intrinsic or acquired resistance of cancerous cells to products. Indeed, it has been observed that cancerous cells from numerous patients suffering from cancer become or are resistant to anti-cancer agents, resulting in the occurrence of new tumoral developments in the patient. Digestive epithelioma, melanoma and kidney cancer are examples of innate chemoresistance. Leukaemia, breast cancer and small-cell bronchial cancer in adults and neuroblastoma in children generally respond well at the beginning of treatment but a large proportion of cases become progressively resistant to treatments.

Primary resistance may be linked to transmembrane transport inhibition and pro-drug activation inhibition mechanisms, modifications in the target enzyme, metabolic processes or repair and inactivation phenomena.

Acquired resistance phenomena are multiple. One of these resistances is multidrug resistance (MDR). MDR is associated with a decrease in the intracellular retention of drugs of differing action mechanisms (Chen et al., 1986, Cell 47, 381-389; Krishan et al., 1997, Cytometry 29, 279-285; Riordan et al., 1985, Nature 316, 817-819).

A membrane-related protein, P-glycoprotein or "P-gp", is the phenotypic expression of the MDR gene. This protein acts like a dependent power pump transporting cytotoxic drugs outside the cell before they produce their effects. The expression of said protein induces the tumoral cell to resist high concentrations of cytotoxic agents such as doxorubicin, daunomycin, actinomycin D, vinblastin, vincristin, mitomycin C, etoposide, teniposide, etc. The P-gp protein is expressed in normal cells such as those of the gastro-intestinal tract, liver and kidney, where it is thought to eliminate toxins or drugs. It is also thought to be responsible for the low penetration of numerous drugs in the brain.

Therefore, one of the priorities in cancer research consists of finding effective means to circumvent the expression and efficacy of the multidrug resistance phenotype, so as to limit chemotherapy failures. Several studies have been conducted to find agents which inhibit P-gp-related resistance and restore the anti-tumour activity of the cytotoxic product either partially or entirely. Such agents are known as chemosensibilisers or P-gp modulators. Said agents act either directly, by interfering, by competition or steric obstruction, on the fixation sites of the cytotoxic agents, or indirectly, by inhibiting the protein responsible via various mechanisms. A whole range of products are capable of inhibiting multidrug resistance, such as calcium channel inhibitors, phenothiazines, quinidine, anti-malaria agents, anti-oestrogen, cyclosporin. However, the toxicity of these products currently limits their clinical use.

In order to overcome this problem, systems to transport specific anti-cancer agents, particularly doxorubicin, using transferrin (Barabas K. et al., 1992; The Journal or Biological Chemistry, 267(13): 9347-9442), dextran (Ueda Y. et al., 1989, Chem. Pharm. Bull., 37(6): 1639-41; Sheldon K. et al., 1989, Anticancer Research, 9(3): 637-642), antibodies (Hurwitz E. et al., 1975, Cancer Research, 35: 1175-1181), microspheres (Rogers K. E. et al., 1983, Cancer Research, 43: 2741-2748; Jeanneson P. et al., 1990, Cancer Research, 50, 1231-1236), polymers (Tokoyama M. et al., 1990, Cancer Research, 50 1693-1700), or protein fragments (Ohkawa K. et al., 1993, British Journal of Cancer, 67: 247-8; Asakura T. et al., 1997, Anticancer Drug, 8(2): 199-203) have been proposed in the prior art. Anti-cancer agent transport means using sequestration in liposomes or nanoparticles (Kruh G. D. and Goldstein L. J., Curr. Opin. Oncol., 5(6): 1029-34; Cuvier C. et al., 1992, Biochemical Pharmacology, 44: 509-517) have also been proposed. However, these systems did not produce satisfactory performances essentially due to their toxicity, a low specificity with respect to cancerous cells, poor storage stability of the finished product and difficult feasibility.

Therefore, the purpose of the present invention is to offer a new, effective and non-toxic means to combat the problem of multidrug resistance. This purpose is achieved through the use of peptides to carry cytotoxic agents to the cancerous target, said peptides also enabling said agents to avoid different resistance mechanisms, particularly the P-gp pump.

Numerous peptides capable of passing through eukaryote membranes very rapidly, such as the following peptides, Protegrin, Antennapedia, Tachyplesin, Transportan, etc. have been described in the prior art.

Of these, some show cytolytic properties. Said peptides, referred to as antibiotic peptides, particularly include Protegrins and Tachyplesins. Protegrins and Tachyplesins are natural antibiotic peptides with a hairpin type structure held by disulphide bridges. Said bridges play an important role in the cytolytic activity observed on human cells.

Depending on their structure, antibiotic peptides can be classified into three main groups:

Alpha amphipatic helical antibiotic peptides: cecropins and maganins (Maloy, W. L. et al., 1995, BioPolymer 37, 105-122).

Beta leafed antibiotic peptides joined by disulphide bridges: defensins (Lehrer, R. I. et al., 1991, Cell 64: 229-230; Lehrer, R. I. et al., 1993, Ann. Rev. Immunol. 11: 105-128), protegrins (Kokryakov, V. N. et al., 1993, FEBS 337: 231-236), tachyplesins (Nakamura, T. et al., 1988, J. Biol. Chem. 263: 16709-16713; Miyata, T et al., 1989, J. Biochem. 106: 663-668.

Destructured chain antibiotic peptides containing numerous bends due to the presence of multiple prolines: bactenecins and PR39 (Frank, R. W. et al., 1991, Eur. J. Biochem. 202, 849-854).

The term protegrins refers to a set of five peptides referred to as PG-1, PG-2, PG-3, PG-4 and PG-5, the sequences of which are given below, closely related and isolated from pig leukocytes (V. N. Kokryakov et al. FEBS lett. 327, 231-236):

PG-1: RGGRLCYCRRRFCVCVGR-NH$_2$ (SEQ ID NO: 1)

PG-2: RGGRLCYCRRRFCICV . . . —NH$_2$ (SEQ ID NO:2)

PG-3: RGGGLCYCRRRFCVCVGR-NH$_2$ (SEQ ID NO:3)

PG-4: RGGRLCYCRGWICFCVGR-NH$_2$ (SEQ ID NO:4)

PG-5: RGGRLCYCRPRFCVCVGR-NH$_2$ (SEQ ID NO:5)

Tachyplesins (Tamura, H. et al., 1993, Chem. Pharm. Bul. Tokyo 41, 978-980), referred to as T1, T2 and T3 and polyphemusins (Muta, T., 1994, CIBA Found. Sym. 186, 160-174), referred to as P1 and P2, the sequences of which are given below, are homologous peptides isolated from the haemolymph of two crabs, *Tachyplesus tridentatus* for the tachyplesins T1, T2 and T3 and *Limulus polyphemus* for the polyphemusins P1 and P2:

P1: RRWCFRVCYRGFCYRKCR-NH$_2$ (SEQ ID NO:6)
P2: RRWCFRVCYKGFCYRKCR-NH$_2$ (SEQ ID NO:7)

Protegrins, tachyplesins and polyphemusins contain a high proportion of basic residue (lysines and arginines) and comprise four cysteines which form two parallel disulphide bridges. These three groups of peptides also show similarities with some defensins, particularly the human defensin NP-1 (Kokryakov, V. N. et al., 1993, Febs Let. 327, 231-236).

In this way, within the scope of this research work, the Applicant discovered that the irreversible reduction of said disulphide bridges makes it possible to obtain linear peptides able to pass through mammalian cell membranes rapidly via a passive mechanism which does not use a membrane receptor. Said linear peptides are non-toxic and free of lytic activity and, as a result, represent a new system for carrying active substances for therapeutic or diagnostic purposes. The research and results related to said linear peptides and their use as vectors of active substances are described in the Applicant's French patent application registered on 12 Aug. 1998 under the No. 97/10297, the content of which is referred to in this disclosure.

Antennapedia group peptides are derived from fruit fly Antennapedia homeodomain transcription factor and are, for example, described in the PCT international patent applications published under Nos. WO91/18981 and WO97/12912. The sequence of said peptides has the specific characteristic of being highly retained in all homeoproteins. Said peptides are composed of three alpha helices and are able to translocate through cell membranes. The smallest fragment of the homeodomain capable of passing through membranes is a peptide comprising 16 amino acids (Prochiantz, 1996, Curr. Opin. In Neurob. 6, 629-634; Derossi et al., 1994, J. Biol. Chem. 269, 10444-10450).

The research work conducted within the scope of the present invention has now enabled the applicant to demonstrate that said linear peptides, i.e. peptides free of disulphide bridges, may be used as a very effective system to carry an anti-cancer substance to a target and enable said substance to pass through the cell membrane to lead it to a cellular compartment such as the cytoplasm or nucleus. Moreover, surprisingly, the Applicant discovered, in addition to their properties as vectors, some of said peptides can be used to prevent the expression of intrinsic or acquired resistance of cancerous cells with respect to said agents, hereafter referred to as chemoresistance, particularly to combat the problem of multidrug resistance (MDR) and enable said agent to avoid the P-gp pump.

Therefore, the invention more particularly relates to a pharmaceutical composition for treating and/or preventing cancer comprising at least one anti-cancer agent, characterised in that said anti-cancer agent is associated in the composition with at least one peptide capable of carrying said agent into the cancerous cells and preventing the occurrence of chemoresistance to said agent, said peptide complying with one of the following formulas I, II or III:

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16} \quad \text{I}$$

wherein formula I, the residues $X_1$ to $X_{16}$ are amino acid residues, 6 to 10 of which are hydrophobic amino acids and $X_6$ is tryptophan,

BXXBXXXXBBBXXXXXXB II

BXXXBXXXBXXXXBBXB III, wherein formulas II and III:

the identical or different B groups represent an amino acid residue in which the lateral chain comprises a basic group, and the identical or different X groups represent an aliphatic or aromatic amino acid residue, where the retro form of said formula I, II, III peptides, composed of D and/or L configuration amino acids, or a fragment of said amino acids composed of a sequence of at least 5 and, preferentially, at least 7 successive amino acids of formula I, II or III peptides, provided, of course, that said fragment shows properties as vectors that are non-toxic for the cells.

Formula I peptides are derived from the Antennapedia group. In formula I peptides, the hydrophobic amino acids are alanine, valine, leucine, isoleucine, proline, phenylalanine, tryptophan, tyrosine and methionine, and the other amino acids are:

non-hydrophobic amino acids which may be non-polar amino acids such as glycine, or polar amino acids such as serine, threonine, cysteine, asparagine, glutamine, or acidic amino acids (aspartic or glutamic acid), or basic amino acids (lysine, arginine or histidine), or a combination of amino acids of these three categories.

Among the formula I peptides, those comprising 6 hydrophobic amino acids and 10 non-hydrophobic amino acids are preferred.

Formula II linear peptides are derived from the Protegrin group and formula III linear peptides are derived by the Tachyplesin group. Among the formula II and III peptides, the following type are preferred, wherein:

B is selected from arginine, lysine, diaminoacetic acid, diaminobutyric acid, diaminopropionic acid, ornithine, and X is selected from glycine, alanine, valine, norleucine, isoleucine, leucine, cysteine, cysteine$^{Acm}$, penicillamine, methionine, serine, threonine, asparagine, glutamine, phenylalanine, histidine, tryptophan, tyrosine, proline, Abu, carboxylic amino-1-cyclohexane acid, Aib, carboxylic 2-aminotetraline, 4-bromophenyalanine, tert-Leucine, 4-chlorophenylalanine, beta-cyclohexyalanine, 3,4-dichlorophenylalanine, 4-fluorophenyalanine, homoleucine, beta-homoleucine, homophenyalanine, 4-methylphenyalanine, 1-naphthyalanine, 2-naphthyalanine, 4-nitrophenyalanine, 3-nitrotyrosine, norvaline, phenylglycine, 3-pyridyalanine, [2-thienyl]alanine.

In formula I, II or III peptides, B, X and $X_1$ to $X_{16}$ may be natural amino acids or not, including D configuration amino acids.

Preferred peptides used according to the inventions are selected from those with the following amino acid sequences:
RGGRLSYSRRRFSTSTGR (SEQ ID NO:11)
RGGRLSYSRRRFSVSVGR (SEQ ID NO:12)
KWSFRVSYRGISYRRSR (SEQ ID NO:13)
RRLSYSRRRF (SEQ ID NO:14)
Rqikiwfqnrrmkwkk (SEQ ID NO:15)
CENIKIWLSLRSYLKRR (SEQ ID NO:16)
RGGRLAYLRRRWAVLVGR (SEQ ID NO:17)
where the lower case letters represent D configuration amino acids.

The association of an anti-cancer agent and a peptide defined above in the compositions according to the invention advantageously consists of a link which may be produced by any acceptable linking means given the chemical nature, size and number of associated anti-cancer agents and peptides. It may consist of a covalent, hydrophobic or ionic bond, that may or may not be split in physiological media or inside the cell.

The link may be produced at any of the peptide's sites, in which functional groups such as —OH, —SH, —COOH, $NH_2$ are naturally present or have been introduced. In this way, an anti-cancer agent can be linked with the peptide at the N-terminal or C-terminal ends or on the peptide's lateral chains.

Similarly, the link may be produced at any site of the active agent, where, for example, functional groups such as —OH, —SH, —COOH, $NH_2$ are naturally present or have been introduced.

In this way, the invention relates to the use of compounds complying with the following formula IV:

$$A(-)_m(B)_n \qquad \text{IV}$$

where
A represents a peptide as defined above,
B represents an anti-cancer agent,
n is 1 or more, preferably up to 10 and advantageously up to 5,
$(-)_m$ represents the linker between A and B, where m is 1 or more, preferably up to 10 and advantageously up to 5,
to prepare a drug for treating and/or preventing cancer without inducing chemoresistance.

Formula IV compounds may be prepared chemically or using molecular biology techniques.

For the chemical synthesis, commercial devices enabling the incorporation of non-natural amino acids, such as D enantiomers and residue with lateral chains with different hydrophobicities and sizes than those of their natural counterparts, may be used. During synthesis, it is of course possible to make a wide range of modifications, for example, introduce a lipid such as prenyl or myristyl on the N-terminal, so as to be able to fix the peptide according to the invention and therefore the formula IV compound to a lipidic membrane such as that of a liposome composed of lipids. It is also possible to replace one or more (—CO—NH—) peptide linkers by equivalent structures such as —CO—N($CH_3$)—, $CH_2$—$CH_2$—, CO—$CH_2$, or insert groups such as —$CH_2$—, —NH—, —O—.

It is also possible to obtain formula IV compounds or a protein component thereof from a nucleic acid sequence coding for said compound. The present invention also relates to a nucleic acid molecule comprising or composed of a nucleic sequence coding for an antibiotic peptide derived linear peptide. More particularly, the invention relates to a nucleic acid molecule comprising at least one sequence coding for a formula IV compound or a protein component thereof. Said nucleic acids may be DNA or RNA and be associated with control sequences and/or inserted in vectors. The vector used is selected according to the host in which it is to be transferred; it may be any vector such as a plasmid. Said nucleic acids and vectors are useful to produce peptides and formula IV compounds or a protein component thereof in a cellular host. The preparation of said vectors and the production or expression of peptides or formula IV compounds in a host may be performed using molecular biology and genetic engineering techniques well known to specialists in the art.

As mentioned above, research work has surprisingly revealed that the peptides defined above are able not only to carry the anti-cancer agent to the cancerous cells, but also to prevent the occurrence of chemoresistance to said agent. As a result, the invention also relates to an inhibition process of the potential ability of an anti-cancer agent to induce chemoresistance in a subject who has received said agent, consisting of associating said agent with at least one formula I, II or III peptide by any suitable means, particularly those described above.

Therefore, the invention also relates to the use of a formula IV compound such as that defined above to prepare an anti-cancer drug also capable of preventing the occurrence of chemoresistance.

According to a preferred embodiment of the above use, said peptide is associated in the drug with the anti-cancer agent by a linker such as that described above. Preferentially, said linker can be split selectively in the cellular environment. Said drug comprises a pharmaceutically acceptable vehicle compatible with the adopted administration method.

The anti-cancer agents used within the scope of the present invention are all those that are used or can be used in chemotherapy, such as, not exhaustively, doxorubicin, daunomycin, actinomycin D, vinblastin, vincristin, mitomycin C, etoposide, teniposide, taxol, taxoter, methotrexate, etc. Naturally, the invention more particularly relates to anti-cancer agents for which occurrences of chemoresistance have already been observed in exposed subjects.

Within the exposed scope of the present invention, the term anti-cancer agent refers to active substances against P-gp and the gene coding for it, more particularly antibodies or antibody components, nucleic acids or oligonucleotides or ribozymes. Indeed, the present invention also relates to the association of reverse oligonucleotides with the peptides described above to inhibit the expression of P-gp, therefore, useful for treating or preventing cancer while preventing the multidrug resistance phenomenon.

The compositions according to the invention containing formula IV compounds and advantageously a pharmaceutically acceptable vehicle may be administered by different routes including (non-exhaustively), the intravenous, intramuscular, subcutaneous routes, etc.

Other advantages and characteristics of the invention can be seen in the following examples related to the preparation of formula IV compounds where the anti-cancer agent is doxorubicin and the effect of carrying doxorubicin on its internalisation.

Experimental Conditions
Chemical Synthesis

Several peptides were produced and their internalisation was tested in several cell lines. As a general rule, the physicochemical properties of the peptides were modified and the results obtained demonstrate that, depending on the modification, some peptides show improved penetration over others, such as the peptides of compounds No. 1 to 6 of table I below. It was also observed that some peptides penetrate more rapidly in one cell type than in others, indicating cellular tropism.

Preparation of Doxorubicin-Succ-Peptides

Figure 1:
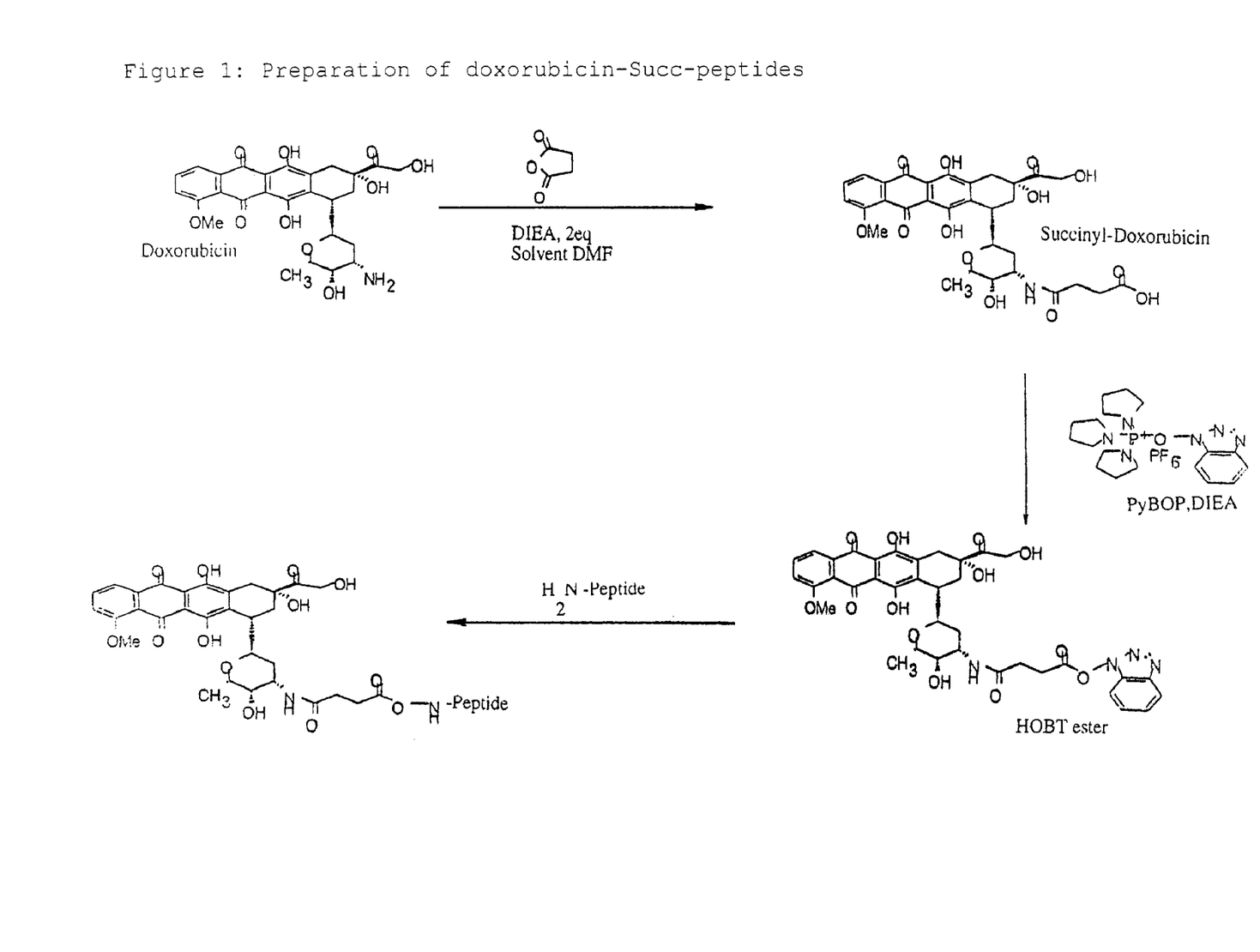
FIG. 1. A diagram showing the synthesis of doxorubicin-Succ-peptides.

As shown in the synthesis diagram in FIG. 1, the bonding of doxorubicin on a peptide by means of the succinic link is performed in 3 steps:

Succinic anhydride (1.1 eq, dissolved in DMF) is added to doxorubicin hydrochloride (1 eq), dissolved in dimethylformamide (DMF) in the presence of Diisopropylethylamine (DIEA, 2 eq).

After an incubation period of 20 min at ambient temperature, the doxorubicin hemisuccinate formed in this way is then activated by adding PyBOP (1.1 eq Benzotriazol-1-yl-oxypyrrolidinephosphonium Hexafluorophosphate in DMF) and DIEA (2 eq). This second reaction mixture is incubated for 20 min.

The peptide (1.2 eq in DMF) is then added to the reaction mixture and spontaneously bonds with the doxorubicin hemisuccinate activated during an additional incubation period of 20 min.

The linker is then purified on preparative HPLC (High Pressure Liquid Chromatography) and then freeze-dried.

Each of the steps and the final product are tested using analytical HPLC and mass spectrometry.

Preparation of Doxorubicin-SMP-3 MP-Peptide.

Figure 2:
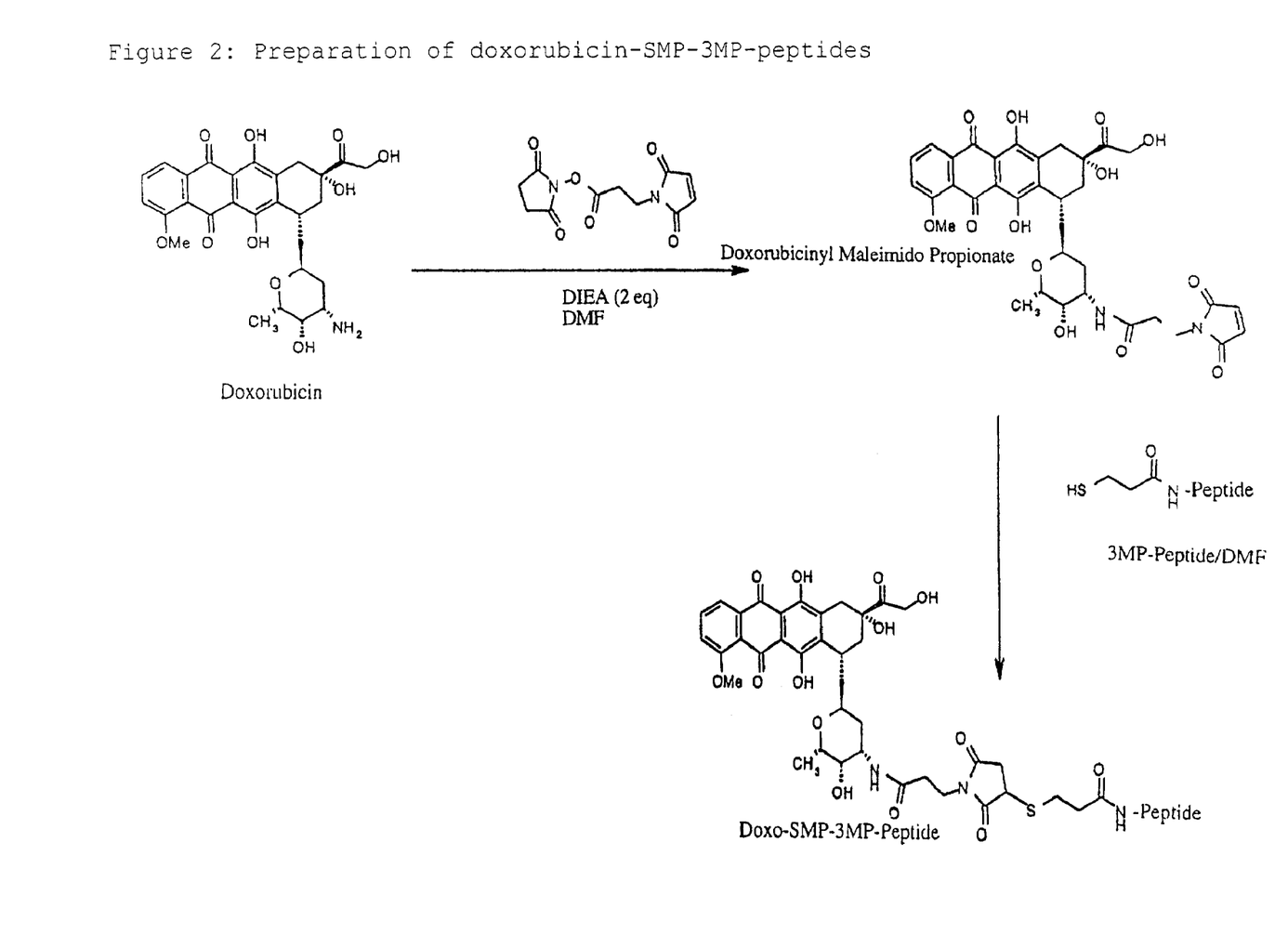
FIG. 2. A diagram showing the synthesis of doxorubicin-SMP-3 MP-peptides.

As shown in the synthesis diagram in FIG. 2, the bonding of doxorubicin on a peptide carrying a thiol function is performed in 2 steps:

N-hydroxy-Succinimidyl-Maleimido-Propionate (SMP, 1 eq, dissolved in DMF) is added to doxorubicin hydrochloride (1 eq), dissolved in dimethylformamide (DMF) in the presence of Diisopropylethylamine (DIEA, 2 eq).

The peptide carrying a thiol function (1.2 eq in DMF) is then added to the reaction mixture and spontaneously bonds onto the doxorubicin maleimidopropionate during an additional incubation period of 20 min.

The linker is then purified on preparative HPLC (High Pressure Liquid Chromatography) and then freeze-dried.

Each of the steps and the final product are tested using analytical HPLC and mass spectrometry.

Tested Products

The tested products are given in table I below.

TABLE I

| Compound | | SEQ ID NOs |
|---|---|---|
| 1 | doxo-CO-(CH2)$_2$-CO-RGGRLSYSRRRFSTSTGR | RGGRLSYSRRRFSTSTGR SEQ ID NO:11 |
| 2 | doxo-CO-(CH2)$_2$-CO-RGGRLSYSRRRFSVSVGR | RGGRLSYSRRRFSVSVGR SEQ ID NO:12 |
| 3 | doxo-CO-(CH2)$_2$-CO-KWSFRVSYRGISYRRSR | KWSFRVSYRGISYRRSR SEQ ID NO:13 |
| 4 | doxo-CO-(CH2)$_2$-CO-RRLSYSRRRF | RRLSYSRRRF SEQ ID NO:14 |
| 5 | doxo-SMP-3MP-rqikiwfgnrrmkwkk | rqikiwfgnrrmkwkk SEQ ID NO:15 |
| 6 | doxo-SMP-CENIKIWLSLRSYLKRR | CENIKIWLSLRSYLKRR SEQ ID NO:16 |
| 7 | doxo-CO-(CH2)$_2$-CO-RGGRLAYLRRRWAVLVGR | RGGRLAYLRRRWAVLVGR SEQ ID NO:17 | doxo = doxorubicin
CO-(CH2)$_2$-CO = Succinate linker
SMP-3MP = SuccinimydylMaleimido-Propionate-3-MercaptoPropionate linker doxo=doxorubicin
CO—(CH2)$_2$—CO=Succinate linker
SMP-3MP=SuccinimydylMaleimido-Propionate-3-MercaptoPropionate linker Cell Culture The susceptible K562 chronic myeloid leukaemia cells, resistant K562/ADR cells and HL60/R10 promyeloid leukaemia cells are of human origin and were obtained commercially from the ATCC. The cells are inoculated at a rate of approximately $10^4$ cells per well, 24 hours before adding the products. The cells are kept in culture at 37° C. in an atmosphere at 95% humidity and 5% $CO_2$ in an OptiMem medium.

Internalisation

The susceptible K562 cells and resistant K562/ADR cells are incubated either with free doxorubicin or with doxorubicin in a vector at a concentration of 3 µM. After 30 minutes of incubation at 37° C., the cells are washed three times with PBS. The internalisation of the products is then analysed by flow cytometry. The samples are analysed with a flow cytometer equipped with a 15 mA argon laser. The fluorescence emitted is recorded on a logarithmic scale at (575 NM) nm after an excitation at (488) nm. The fluorescence is measured on 10,000 cells selected according to the size SS and granulosity FS parameters. The results are expressed as a percentage of positive cells of the fluorescence intensity logarithm. The results are analysed using the software program Cell Quest.

Cytotoxicity

The susceptible K562 cells and resistant K562/ADR cells are incubated either with free doxorubicin or with doxorubicin in a vector at increasing concentrations after 48 hours in culture in the presence of the products. At the end of the culture period, MTT (3-(4,5-dimethylthiazole-2-yl)-2,5-diphenyltetrazolium bromide) is added into the wells and the culture plates are then incubated for 4 hours in the incubator. The resulting crystalline formazan deposit is then dissolved by adding 200 µl of DMF/SDS. The optical density (OD) is measured at 550 nm (reference 630 nm) using a microplate reader.

The graphic representation of the OD percentages of the wells treated as a function of the concentration of products is used to determine the $IC_{50}$ which corresponds to the concentration of product that inhibits 50% of growth.

The $IC_{50}$ values are used to quantify the resistance factor (F. Res) of the resistant lines using the following ratio:

$$F.\ Res = \frac{\text{Cytotoxic } IC_{50} \text{ for resistant line}}{\text{Cytotoxic } IC_{50} \text{ for susceptible parental line}}$$

The reversion factor (F. Rev) corresponds to the effect of a modulator (the vector) on the susceptibility of the cells to the anti-tumour agents according to the following ratio:

$$F.\ Rev = \frac{\text{Cytotoxic } IC_{50} \text{ alone}}{\text{Cytotoxic } IC_{50} \text{ in vector}}$$

Results

Internalisation

Figure 3:
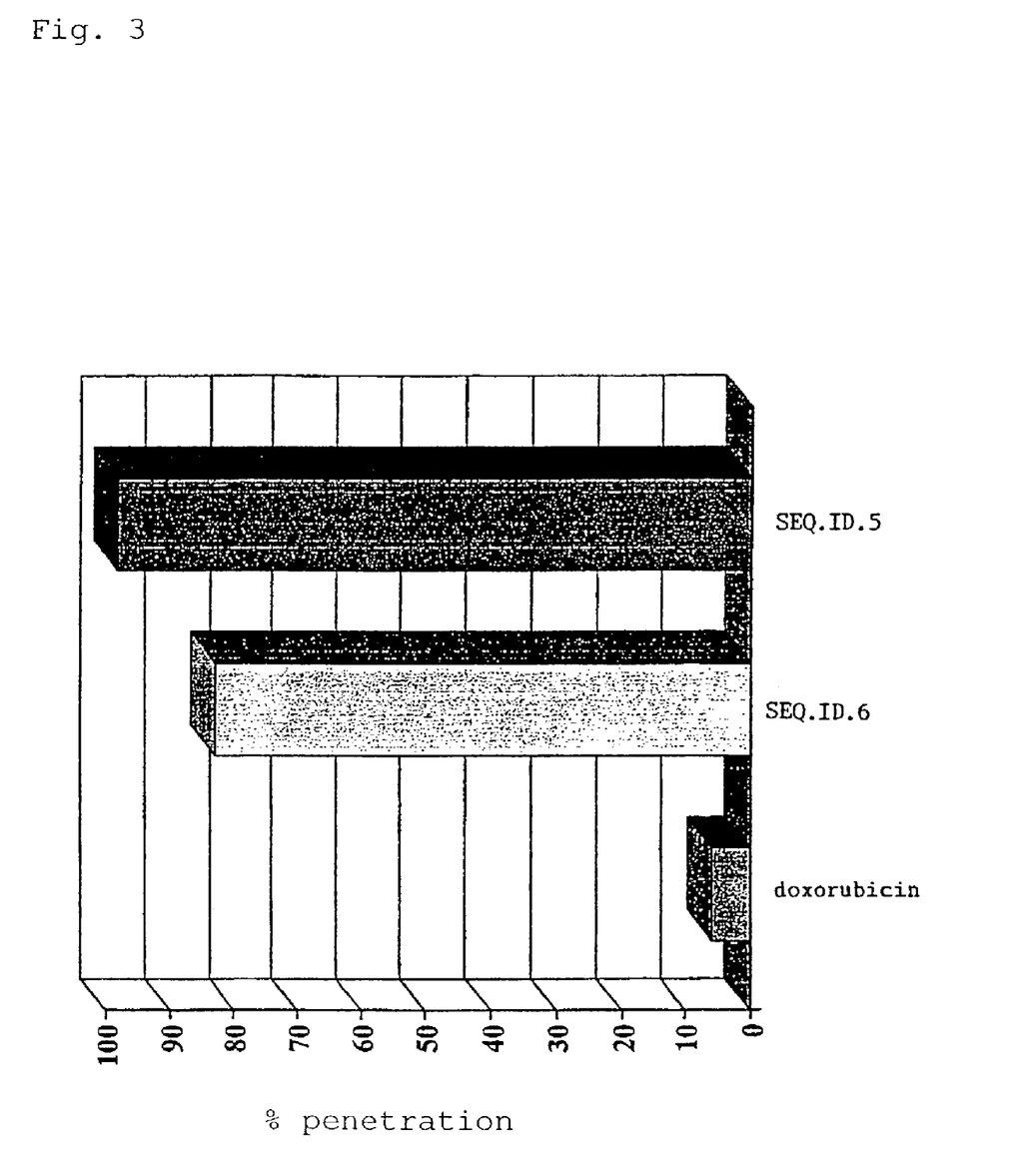
FIG. 3. A result of the internalization experiments for the susceptible K562 and resistant K562/ADR cells. The cells were incubated either with free doxorubicin or with doxorubicin in a vector. In the resistant K562/ADR cells, 5.68% of the cells are positive, while in the cells incubated with doxorubicin in a vector, 98% of the cells are positive, indicating the improved penetration.

The susceptible K562 cells and resistant K562/ADR cells are incubated either with free doxorubicin or with doxorubicin in the vector. After 30 min of incubation, the internalisation of the products is measured by flow cytometry. FIG. 3 in the appendix shows that, in the resistant K562/ADR cells, only 5.86% of the cells are positive, while with the vector (e.g.

in the form of compound No. 5 in table I), 98% of the cells are positive, indicating a marked improvement in penetration.

Cytotoxicity

The susceptibility of the cells to anti-tumour agents was measured using the MTT test under the experimental conditions defined above wherein the relationship between the optical density and the number of viable cells is linear.

Figure 4:
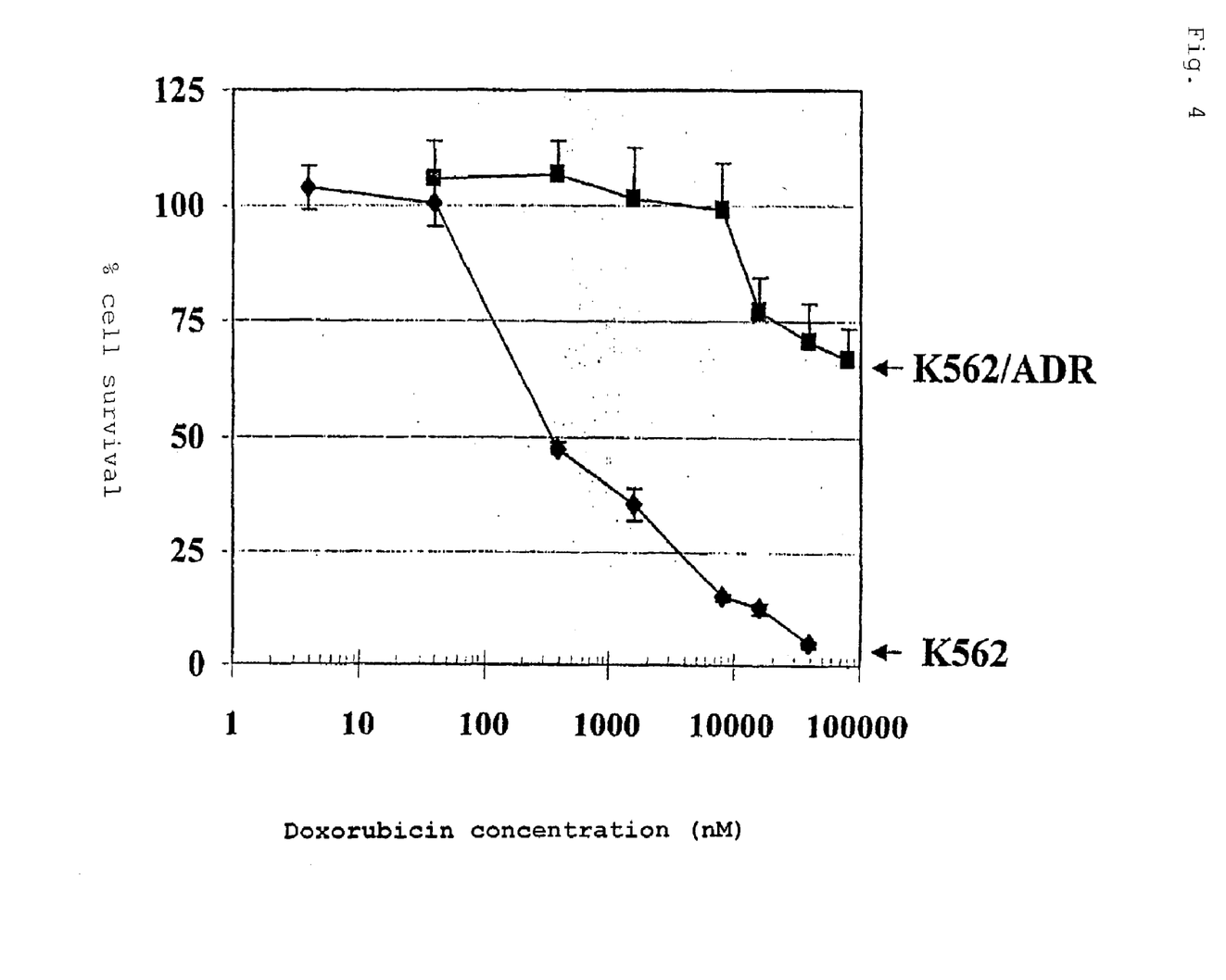
FIG. 4. Measuring the susceptibility of cells to anti-tumor agents using the MTT test. The activity of doxorubicin in the susceptible cells (K562) and in the resistant cells (K562/ADR) is shown. The graphic shows that the K562/ADR cells are resistant to doxorubicin.

The activity of doxorubicin in the susceptible cells (K562) and in the resistant cells K562/ADR was first of all observed. The cells are incubated with increasing concentrations of doxorubicin and after 24 hours of incubation, the survival of the cells is measured using the MTT test. As shown in FIG. 4, the K562/ADR cells are indeed resistant to doxorubicin. For example, at a concentration of 8 µM, only 15% of the susceptible cells survive while 100% of the resistant cells survive.

The cytotoxicity of doxorubicin in the vector was then analysed. Table II below represents the concentration of product inducing 50% growth inhibition $IC_{50}$ determined on the susceptible line K562 and the resistant line K562/ADR

TABLE II

| Lines | K562 | K562/ADR | F. Res | F. Rev |
|---|---|---|---|---|
| Free Doxo | 0.9 µM | 25 µM | 28 | |
| Compound 1 | 15 µM | 5-10 µM | 0.7 | 2.5 |
| Free Doxo | 0.15 µM | 15.5 µM | 100 | |
| Compound 2 | 3.6 µM | 3.2 µM | 0.9 | 5 |
| Free Doxo | 0.45 µM | 65 µM | 144 | |
| Compound 3 | 2 µM | 1.5 µM | 0.8 | 43 |
| Free Doxo | ND | 55 µM | | |
| Compound 4 | 20 µM | 20 µM | 1 | 2.8 |
| Free Doxo | 0.4 µM | 70 µM | 175 | |
| Compound 5 | 1.5 µM | 2 µM | 1.3 | 35 |
| Free Doxo | 0.3 µM | 70 µM | 233 | |
| Compound 6 | 5 µM | 5.5 µM | 1.1 | 12.8 |
| Free Doxo | 0.1 µM | >78 µM | >780 | |
| Compound 7 | 3.5 µM | 3 µM | 0.85 | >26 |

These results show that the K562/ADR cells are indeed resistant to doxorubicin alone. Carrying the doxorubicin in a peptide-vector makes it possible to circumvent the problem of multidrug resistance. For example, in one case, the $IC_{50}$ of free doxorubicin in the resistant cells is 70 µM, while with the vector (compound 5), the $TC_{50}$ is only 2 µM.

These results also show that the products in vectors are not excreted by the P-gp pump since the same $IC_{50}$ is obtained in the susceptible cells and resistant cells and the resistance factor is almost 1.

Figure 5:
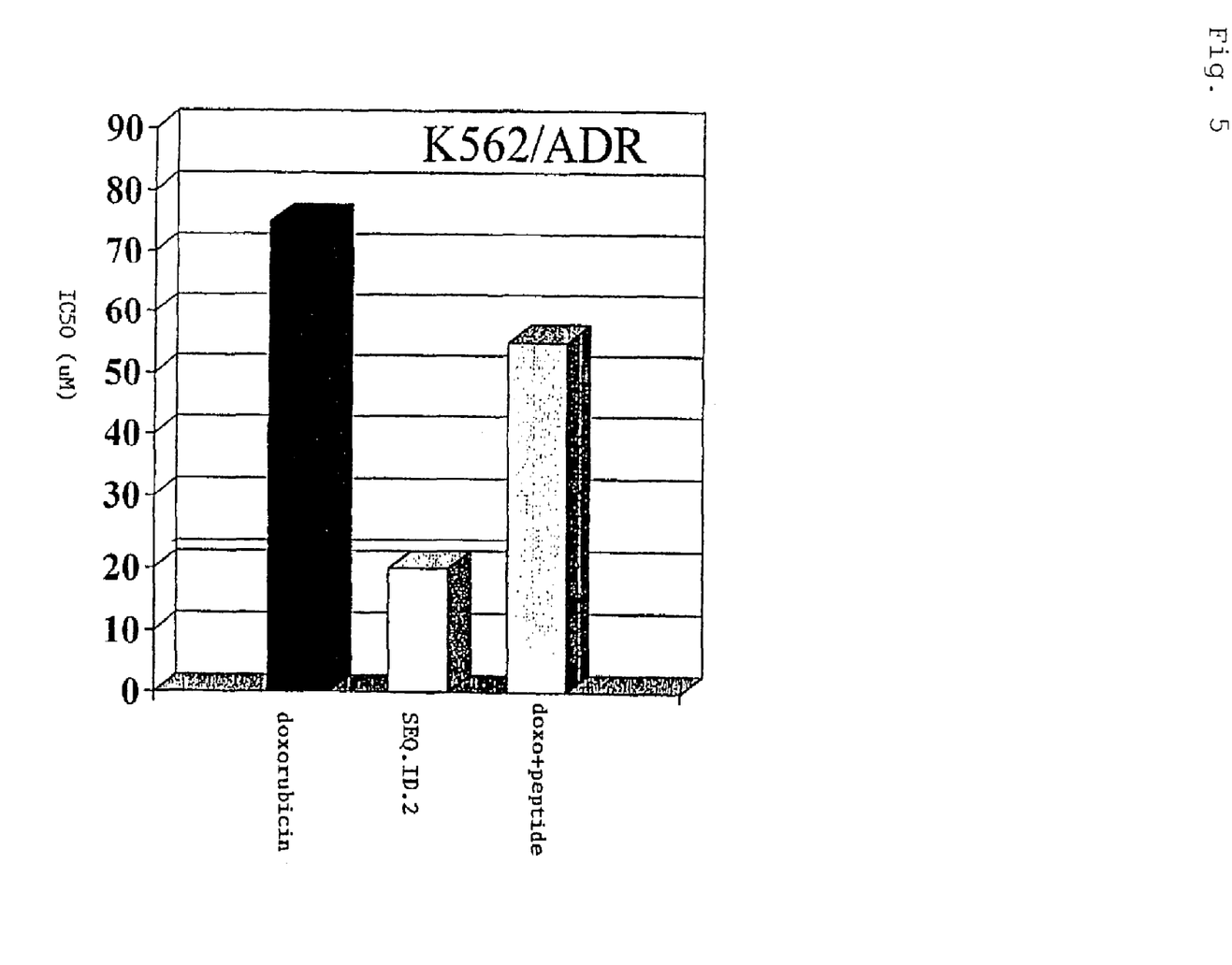
FIG. 5. Comparison of the activity of doxorubicin in a vector (compound SEQ ID NO:2) with doxorubicin added to but not linked with the peptides. The graphic shows that the $IC_{50}$ of doxorubicin in the vector is 19 µM, while that of doxorubicin added to the vector is about 50 µM.

To be certain that the cytotoxicity observed for doxorubicin in vectors is not due to the peptide alone, an experiment was conducted, comparing the activity of doxorubicin in the vector (compound 2) with doxorubicin added to, but not linked with, the peptide. FIG. 5 appended shows that the $IC_{50}$ of doxorubicin in the vector (compound 2) is 19 µM while that of doxorubicin added to the vector is approximately 50 µM, thus demonstrating the need to introduce a vector to reduce cell resistance.

The same type of experiment was conducted on another cell line resistant to doxorubicin HL60/R1. The cytotoxicity results in the HL60 cells with compound No. 2 are given in table III below.

TABLE III

| | HL60/R10 | F. Rev |
|---|---|---|
| Free doxo | 40 µm | |
| Compound No. 2 | 25 µm | 1.6 |

The invention claimed is:

1. A pharmaceutical composition comprising at least one anti-cancer agent bonded to a peptide, said peptide consisting of the amino acid sequence of SEQ ID NO:14, and a pharmaceutically acceptable carrier.

* * * * *